(12) United States Patent
Harrison

(10) Patent No.: US 9,615,800 B2
(45) Date of Patent: Apr. 11, 2017

(54) EVIDENCE BASED INTERACTIVE MONITORING DEVICE AND METHOD

(71) Applicant: Michael John Harrison, Wellington (NZ)

(72) Inventor: Michael John Harrison, Wellington (NZ)

(73) Assignee: MIMAR LP (NZ)

(*) Notice: Subject to any disclaimer, the term of this patent is extended or adjusted under 35 U.S.C. 154(b) by 51 days.

(21) Appl. No.: 14/391,011

(22) PCT Filed: Apr. 29, 2013

(86) PCT No.: PCT/IB2013/053361
§ 371 (c)(1),
(2) Date: Oct. 7, 2014

(87) PCT Pub. No.: WO2013/164747
PCT Pub. Date: Nov. 7, 2013

(65) Prior Publication Data
US 2015/0065816 A1     Mar. 5, 2015

(30) Foreign Application Priority Data

Apr. 30, 2012 (NZ) .......................................... 598246
Apr. 24, 2013 (NZ) .......................................... 609832

(51) Int. Cl.

| | | |
|---|---|---|
| *A61B 5/00* | (2006.01) | |
| *A61B 5/0295* | (2006.01) | |
| *A61B 5/0402* | (2006.01) | |
| *A61B 5/1455* | (2006.01) | |
| *A61B 5/0205* | (2006.01) | |
| *A61B 5/021* | (2006.01) | |
| *A61B 5/024* | (2006.01) | |
| *A61B 5/08* | (2006.01) | |
| *A61B 5/01* | (2006.01) | |

(Continued)

(52) U.S. Cl.
CPC ............ *A61B 5/746* (2013.01); *A61B 5/0002* (2013.01); *A61B 5/02055* (2013.01); *A61B 5/0295* (2013.01); *A61B 5/0402* (2013.01); *A61B 5/14551* (2013.01); *A61B 5/4821* (2013.01); *A61B 5/6803* (2013.01); *A61B 5/7203* (2013.01); *A61B 5/7246* (2013.01); *A61B 5/7275* (2013.01); *A61B 5/741* (2013.01); *A61B 5/743* (2013.01); *A61B 5/7455* (2013.01); *A61B 5/01* (2013.01); *A61B 5/021* (2013.01); *A61B 5/022* (2013.01); *A61B 5/024* (2013.01); *A61B 5/0205* (2013.01); *A61B 5/0215* (2013.01); *A61B 5/02405* (2013.01); *A61B 5/0816* (2013.01); *A61B 5/7264* (2013.01); *A61B 5/7282* (2013.01)

(58) Field of Classification Search
CPC ...................................................... A61B 5/746
USPC .................................................. 600/300, 301
See application file for complete search history.

*Primary Examiner* — John R Downey
(74) *Attorney, Agent, or Firm* — Galbreath Law Offices, P.C.; John A. Galbreath

(57) ABSTRACT

A method for issuing an alert which includes the following steps:—carry out an R analysis on two or more physiological variable inputs;—carry out an N analysis on a primary physiological variable input;—issue an alert if the R analysis confirms a trend for each of the physiological variable inputs and the N analysis shows a statistically significant change in the primary physiological variable input; where the two or more physiological variable inputs include systolic or mean blood pressure and pulse volume, and the primary physiological variable input is systolic or mean blood pressure; such that the alert is a visual, audio, vibratory, tactile or a combination of two or more of these or an alert signal to an output unit configured to output the alert in one of those forms.

25 Claims, 3 Drawing Sheets

(51) Int. Cl.
*A61B 5/0215* (2006.01)
*A61B 5/022* (2006.01)

EVIDENCE BASED INTERACTIVE MONITORING DEVICE AND METHOD

TECHNICAL FIELD

The present invention relates to a data monitoring device and method for monitoring a patient's condition for vital sign variations which require intervention or investigation which do not rely purely on threshold values.

BACKGROUND ART

The use of individual vital sign monitoring by individual instruments to assess patient condition has existed for many decades.

Many vital sign variables such as heart rate, blood pressure, pulse pressure and pulse volume are routinely monitored in modern medicine, especially before, during or after an operation. These variables may be displayed numerically or graphed to allow a medical professional to assess the absolute as well as rate or magnitude of change over time of these variables.

Present anaesthetic monitors often include threshold alarms with fixed default values and/or user adjustable values to alert an anaesthetist when the threshold value has been exceeded. Unfortunately, though the fact a threshold has been exceeded is important, it is not necessarily indicative of a problem unless supported by a change in other vital signs, trends or visual observations, and as such many alerts are simply false alarms. The frequency of false alerts means these threshold alarms can be either turned off or ignored, the anaesthetist relying on careful monitoring to react to important changes. The interpretation of the monitor output, and changes over time, depend on the skill and experience of the anaesthetist.

An additional problem with threshold alarms is that the relevant threshold value may change during an operation as other variables change. In addition the relevant threshold often depends on the patient concerned and as such for certain patients a default threshold may be inappropriate. This means that the setting of the threshold value, if not locked to a default, depends on the skill and experience of the anaesthetist.

A further problem with many sensors or monitoring devices is the difference in data collection rates each provide. Some sensors and/or monitoring devices provide a nearly continuous data stream, others provide an output many times a second and still others every second, every minute or longer. This variation in data output rates can make it difficult to combine data from a multitude of monitoring devices, certainly it can require a great deal of skill. In fact for some monitoring devices the data collection frequency may not be apparent or disclosed.

Any discussion of the prior art throughout the specification is not an admission that such prior art is widely known or forms part of the common general knowledge in the field.

DISCLOSURE OF INVENTION

It is an object of the present invention to provide an alternative to threshold alarm monitors.

The present invention provides a method for issuing an alert which includes the following steps:
carry out an R analysis on two or more physiological variable inputs;
carry out an N analysis on a primary physiological variable input;
issue an alert if the R analysis confirms a trend for each of the physiological variable inputs and the N analysis shows a statistically significant change in the primary physiological variable input;
where the two or more physiological variable inputs include systolic or mean blood pressure and pulse volume, and the primary physiological variable input is systolic or mean blood pressure;
and the R-analysis includes the following steps in order:
  i. buffer each physiological variable input for a physiological variable R time period, where the physiological variable R time period finishes at a current time, creating buffered physiological variable data for each vital sign input;
  ii. determine a physiological variable median from each set of buffered physiological variable data;
  iii. compare a current physiological variable value, which is the physiological variable input at the current time, with the respective physiological variable median to determine a physiological variable difference for each physiological variable;
  iv. wait a predetermined time, a physiological variable R2 time interval, and carry out steps (i) to (iii) until at least 3 physiological variable differences for each physiological variable have been calculated;
  v. compare each physiological variable difference for each physiological variable and if three or more consecutive physiological variable differences for each physiological variable input are in the same direction from the respective physiological variable median then a trend is confirmed;
such that for the R-analysis each physiological variable R time period includes at least 10 measurements of the physiological variable in question and the physiological variable R time period is at least 100 seconds,
and the N-analysis includes either
  steps (vi) to (viii) in order, or
  steps (ix) and (x) in order:
  vi. buffer the primary physiological variable input for a primary physiological variable N time period, where the primary physiological variable N time period finishes at the current time, creating buffered primary data;
  vii. carry out the following calculations:—

$$(ut1-\bar{u})/(SDu)=V1$$

$$(\Delta u_{(12)}-\Delta\bar{u})/(SD\Delta u)=V2$$

$$Cul=\sqrt{(V1^2+V2^2)}$$

where
t1=time 1;
t2=current time;
ut1 is a value of the primary physiological variable at t1;
$\bar{u}$ is a mean primary physiological value from population data;
$\Delta\bar{u}$ is a mean change in the primary physiological variable from the population data over the period of time between t1 and t2;
$\Delta u_{(12)}$ is a change in the primary physiological variable over the period of time between t1 and t2;
SDu is the standard deviation of the primary physiological variable from the population data;
SD$\Delta$u is the standard deviation of the change in primary physiological variable from the population data over the period of time between t1 and t2;

Cu1 is a combined primary physiological variable indicator;

viii. compare Cu1 value with a predetermined value SS, if Cu1>SS then this confirms a statistically significant change in the primary physiological variable;

such that for steps (vi) to (viii) the N-analysis SS is at least 1, and the time period between t1 and t2 is at least 10 seconds;

ix. buffer the primary physiological variable input for a primary physiological variable N time period, where the primary physiological variable N time period finishes at the current time, creating buffered primary data;

x. carry out a principal component analysis to determine whether, over the time period t2-t1, a statistically significant change has occurred in the primary physiological variable, where t1=time 1, and t2=current time; wherein a statistically significant change has occurred if the principal component analysis confirms that the primary physiological variable is greater than a predetermined number of standard deviations (SS) from that expected in each direction, such that SS is independently chosen for each direction;

such that for steps (ix) and (x) the N-analysis using the principal component analysis method the time period between t1 and t2 is at least 10 seconds and each SS is greater than or equal to 1;

where the alert is a visual, audio, vibratory, tactile or a combination of two or more of these or an alert signal to an output unit configured to output the alert in one of those forms.

The present invention also provides a method for issuing an alert which includes the following steps:

carry out an R analysis on two or more physiological variable inputs;

carry out an N analysis on a primary physiological variable input;

issue an alert if the R analysis confirms a trend for each of the physiological variable inputs and the N analysis shows a statistically significant change in the primary physiological variable input;

where the two or more physiological variable inputs include systolic or mean blood pressure and pulse volume, and the primary physiological variable input is systolic or mean blood pressure;

and the R-analysis includes the following steps in order:

i. buffer each physiological variable input for a physiological variable R time period, where the physiological variable R time period finishes at a current time, creating buffered physiological variable data for each vital sign input;

ii. determine a physiological variable median from each set of buffered physiological variable data;

iii. compare a current physiological variable value, which is the physiological variable input at the current time, with the respective physiological variable median to determine a physiological variable difference for each physiological variable;

iv. wait a predetermined time, a physiological variable R2 time interval, and carry out steps (i) to (iii) until at least 3 physiological variable differences for each physiological variable have been calculated;

v. compare each physiological variable difference for each physiological variable and if three or more consecutive physiological variable differences for each physiological variable input are in the same direction from the respective physiological variable median then a trend is confirmed;

such that for the R-analysis each physiological variable R time period includes at least 10 measurements of the physiological variable in question and the physiological variable R time period is at least 100 seconds, and the N-analysis includes the following steps in order:

vi. buffer the primary physiological variable input for a primary physiological variable N time period, where the primary physiological variable N time period finishes at the current time, creating buffered primary data;

vii. carry out the following calculations:—

$$(ut1-\bar{u})/(SDu)=V1$$

$$(\Delta u_{(12)}-\Delta\bar{u})/(SD\Delta u)=V2$$

$$Cu1=\sqrt{(V1^2+V2^2)}$$

where t1=time 1;

t2=current time;

ut1 is a value of the primary physiological variable at t1;

$\bar{u}$ is a mean primary physiological value from population data;

$\Delta\bar{u}$ is a mean change in the primary physiological variable from the population data over the period of time between t1 and t2;

$\Delta u_{(12)}$ is a change in the primary physiological variable over the period of time between t1 and t2;

SDu is the standard deviation of the primary physiological variable from the population data;

SDΔu is the standard deviation of the change in primary physiological variable from the population data over the period of time between t1 and t2;

Cu1 is a combined primary physiological variable indicator;

viii. compare Cu1 value with a predetermined value SS, if Cu1>SS then this confirms a statistically significant change in the primary physiological variable;

such that for the N-analysis SS is at least 1, and the time period between t1 and t2 is at least 10 seconds;

where the alert is a visual, audio, vibratory, tactile or a combination of two or more of these, or an alert signal to an output unit configured to output the alert in one of those forms.

The present invention also provides the following alternative method for issuing an alert which includes the following steps:

carry out an R analysis on two or more physiological variable inputs;

carry out an N analysis on a primary physiological variable input;

issue an alert if the R analysis confirms a trend for each of the physiological variable inputs and the N analysis shows a statistically significant change in the primary physiological variable input;

where the two or more physiological variable inputs include systolic or mean blood pressure and pulse volume, and the primary physiological variable input is systolic or mean blood pressure;

and the R-analysis includes the following steps in order:

i. buffer each physiological variable input for a physiological variable R time period, where the physiological variable R time period finishes at a current time, creating buffered physiological variable data for each vital sign input;

ii. determine a physiological variable median from each set of buffered physiological variable data;

iii. compare a current physiological variable value, which is the physiological variable input at the current time, with the respective physiological variable median to determine a physiological variable difference for each physiological variable;

iv. wait a predetermined time, a physiological variable R2 time interval, and carry out steps (i) to (iii) until at least 3 physiological variable differences for each physiological variable have been calculated;

v. compare each physiological variable difference for each physiological variable and if three or more consecutive physiological variable differences for each physiological variable input are in the same direction from the respective physiological variable median then a trend is confirmed;

such that for the R-analysis each physiological variable R time period includes at least 10 measurements of the physiological variable in question and the physiological variable R time period is at least 100 seconds, and the N-analysis includes the following steps in order:

vi. buffer the primary physiological variable input for a primary physiological variable N time period, where the primary physiological variable N time period finishes at the current time, creating buffered primary data;

vii. carry out a principal component analysis to determine whether, over the time period t2-t1, a statistically significant change has occurred in the primary physiological variable, where t1=time 1, and t2=current time; wherein a statistically significant change has occurred if the principal component analysis confirms that the primary physiological variable is greater than a predetermined number of standard deviations (SS) from that expected in each direction, such that SS is independently chosen for each direction;

such that for the N-analysis using the principal component analysis method the time period between t1 and t2 is at least 10 seconds and each SS is greater than or equal to 1, where the alert is a visual, audio, vibratory, tactile or a combination of two or more of these, or an alert signal to an output unit configured to output the alert in one of those forms.

Preferably the R-analysis is carried out on at least three physiological variables. In a highly preferred form one of the physiological variables is heart rate, except where the heart rate is being stabilised by mechanical, electro-mechanical or chemical means, or a combination of these. Preferably the heart rate is a median heart rate obtained from three or more different heart rate sources.

Preferably each physiological variable R time period includes at least 20 measurements of the physiological variable in question. In a highly preferred form this is at least 30 measurements.

Preferably the physiological variable R time period is between 100 seconds and 5 minutes. It is preferred that the physiological variable R2 time period is at least 10 seconds Preferably the time period between t1 and t2 is between 15 seconds and 150 seconds The present invention also includes a system including at least one input device, a processing unit and one or more output units where:

the or each input device is configured to measure at least one physiological variable and output a physiological variable input;

the processing unit is configured to directly or indirectly accept each physiological variable input from the or each input device and carry out the method previously described, the processing unit is further configured to output the alert as an alert signal to the or each output unit;

the or each output unit is configured to process the alert signal into the alert for a user in one or more of the following forms visual, audio, tactile or vibrational.

Preferably the or each input device is selected from the list consisting of an electrocardiogram (ECG), a temperature monitor, a pulseoximeter, a non-invasive blood pressure monitor, an invasive blood pressure monitor, a gas analysis monitor, and an anaesthesia monitor connected to one or more of the previously mentioned input devices.

Preferably the processing unit is configured to directly accept the output from the or each input device.

Preferably the processing unit is configured to check each physiological variable input against one or more predetermined value, an artefact value, for that physiological variable input to determine if that physiological variable input is an artefact, where an artefact is a physiological variable input outside that possible for a patient at that time, if an artefact is detected then that physiological variable data is not used for the R-analysis or N-analysis. Preferably if an artefact is detected then an alert is issued.

Preferably the processing unit is configured to suppress equivalent alerts for a predetermined period of time, an alert suppression time. Preferably the alert suppression time is 5 minutes.

Preferably one output device is a visual display unit configured to visually display a representation of the alert. Preferably the visual display unit also displays a representation of the physiological variable input for one or more physiological variable. Preferably the representation is one or more forms selected from the list consisting of icons, words, graphs, colours, visual indicia and combinations of these.

Preferably one output device is a headset configured to deliver an audio alert. Preferably the headset is wirelessly connected to the processing unit. Preferably the audio alert includes an audio description of the alert.

The present invention further includes a processing unit that is configured to be connected, wirelessly or otherwise, to one or more input devices and one or more output devices, such that said processing unit is configured to carry out the method described earlier.

BRIEF DESCRIPTION OF DRAWINGS

By way of example only, a preferred embodiment of the present invention is described in detail below with reference to the accompanying drawings, in which.

Definitions

Forwarded: Is intended to cover the copying or movement of the data, a signal or an item from one place to another by any means (optically, electrically, wirelessly, by wire or physically)

Mm Hg: pressure indication, millimetres of mercury, about 7.5 mm of mercury is 1 kPa and about 51.7 mm of mercury is 1 pound/square inch.

Physiological variable: This is intended to cover any physiological parameter that varies such as systolic invasive arterial pressure, diastolic invasive arterial pressure, heart rate, pulse volume, carbon dioxide level (inspired, end-tidal), respiratory rate, body temperature, non-invasive blood pressure (systolic and/or diastolic), etc.

Steady state data: this for anaesthesia applications is data collected after the respiratory parameters have reached a steady state as this avoids the chaotic physiological changes that occur in the transition between conscious to sedated states.

BEST MODE FOR CARRYING OUT THE INVENTION

Figure 1:
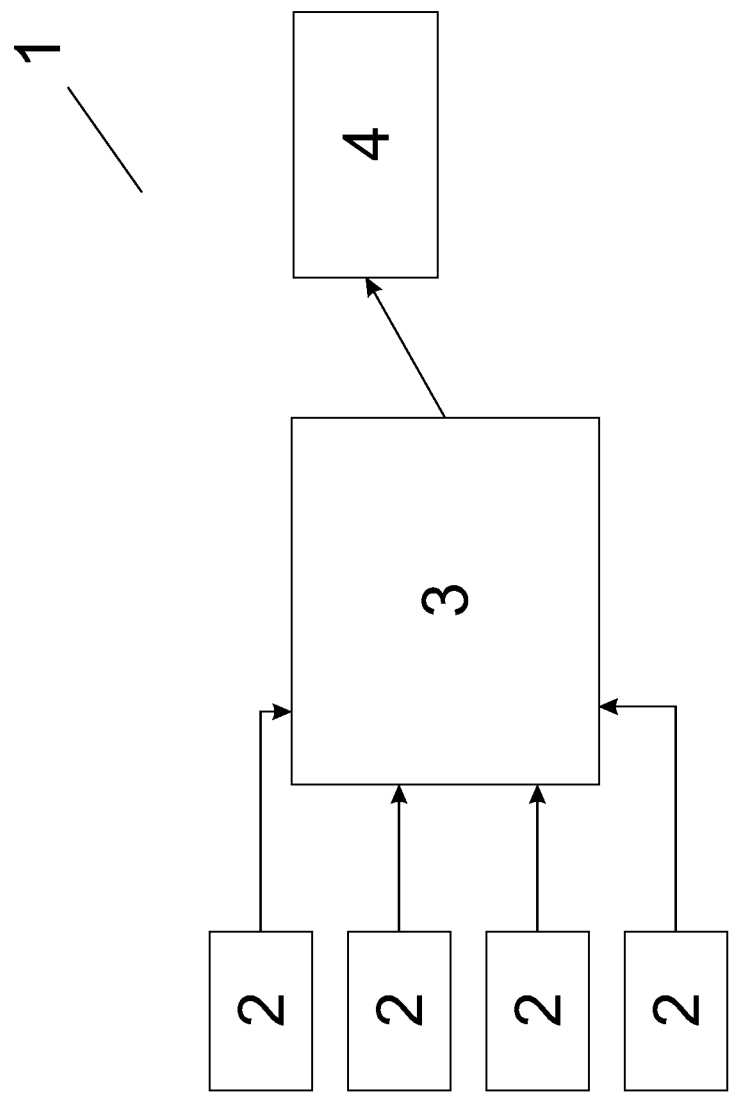
FIG. 1 Is a block diagram of a monitoring system.

Referring to FIG. 1 a monitoring system (1) including a number of input devices (2), a processing unit (3) and an output unit (4) is shown.

Each of the input devices (2) is a device designed to measure a physiological variable of a patient and output a signal representative of this physiological variable. The input device (2) may be a sensor that directly outputs a usable signal or a sensor and pre-processing device that outputs a usable signal. Each of the input devices (2) is of a known type and the term is intended to include standard vital sign monitors, providing the vital sign monitor can supply a usable signal related to a physiological variable.

The processing unit (3) is a device which may be a computer running a computer program that carries out some or all of the method. The processing unit (3) takes the output from one or more input device (2) and processes it to determine if an alert needs to be issued.

The output unit (4) is any device that can display, present or audibly convey an alert to a user. For example an output unit (4) includes, but is not limited to, a monitor, a speaker, a headset, a lamp, a visual display unit, a gauge, a vibration device or similar.

Figure 2:
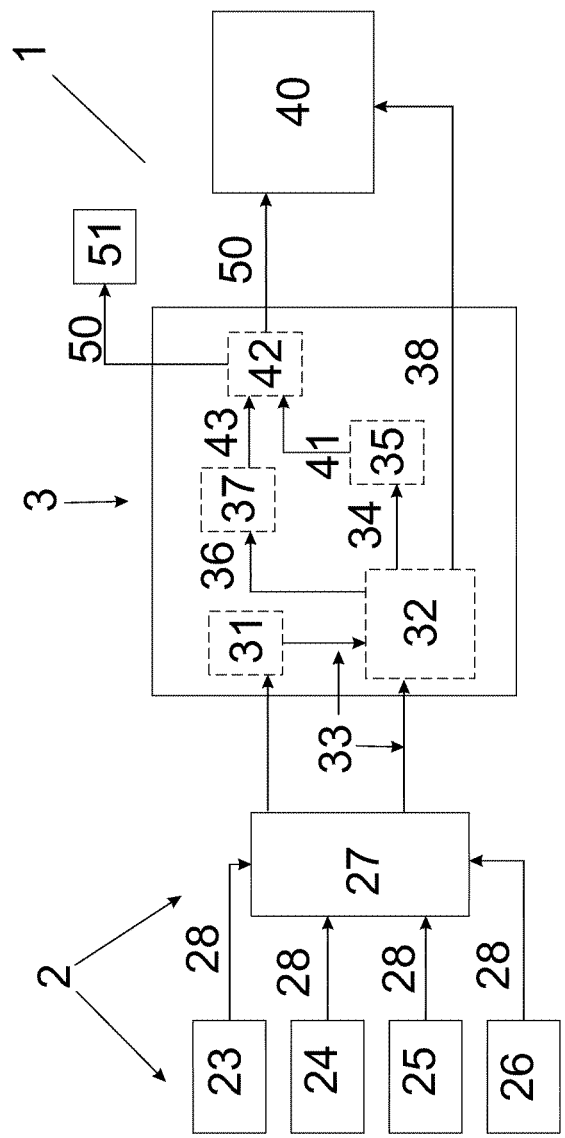
FIG. 2 is the preferred monitoring system.

The preferred form of the monitoring system (1) is shown in FIG. 2, where the input devices (2) are an electrocardiogram (ECG) (23), blood pressure monitor (24), pulseoximeter (25) and gas analysis monitor (26). Where the gas analysis monitor can include both respiratory gas analysis and blood gas analysis, and the blood pressure monitor is an arterial blood pressure monitor.

These input devices (2) are all connected to a further input device (2) which is an anaesthesia monitor (27). The following patient data (28) is transferred from the anaesthesia monitor (27) to the processing unit (3):—
 a. temperature;
 b. systolic blood pressure;
 c. diastolic blood pressure;
 d. mean blood pressure;
 e. ECG heart rate;
 f. Blood pressure monitor heart rate;
 g. pulseoximeter heart rate;
 h. pulseoximeter pulse volume;
 i. gas end tidal (gas Et) $CO_2$;
 j. gas inspired (gas Fi) $CO_2$;
 k. gas respiration rate;
 l. gas end-tidal fraction of anaesthetic agent;

The a temperature sensor collects a, a blood pressure monitor collects b to d and f, the ECG collects e, the pulseoximeter collects g and h, and the gas analysis monitor (26) collects i to l. Noting that in this case the gas analysis monitor (26) is a respiratory gas monitor, in the future essentially real time blood gas analysis may be used (in combination with or instead of a respiratory gas analysis monitor).

The arterial blood pressure is optionally used to calculate a Respiratory Associated Pulse Pressure Variation (RAPPV) in a first processing unit (31) based on the following formula:

$$RAPPV=100\% \times (PPmax-Ppmin)/((Ppmin+Ppmax)/2)$$

Where Ppmax=maximum pulse pressure;
 Ppmin=minimum pulse pressure;

The RAPPV is calculated over a set period, normally between 1 second and 20 seconds with 6-10 seconds being the preferred interval. The calculation of RAPPV is optional but it provides additional information to a user of the system.

The data from the anaesthesia monitor (27) may be collated and sent as a delimited data set (e.g. as a comma delimited dataset in ascii format), partially collated and sent as raw and collated data or simply passed through as raw data. Whatever the format of the data forwarded by the anaesthesia monitor (27) the processing unit (3) is able to convert the data into formatted data. Where formatted data, is data in a suitable format for further processing, using standard means. These standard means include but not limited to analogue to digital convertors, software drivers, signal processing circuitry, frequency counters, etc. Basically 'standard means' is intended to include anything that can convert a raw electrical/optical signal from a sensor or monitoring device to a numerical representation of that signal.

The RAPPV, when calculated, and patient data (28) is forwarded to a main processing unit (32) as incoming data (33). The main processing unit (32) carries out the following steps:—
 i. converts incoming data (33) to formatted data,
 ii. checks for artefacts,
 iii. forwards R formatted data (34) to an R processing unit (35),
 iv. forwards N formatted data (36) to a N processing unit (37),
 v. further processes the formatted data into a form suitable for visual display and forwards this visual data (38) to a visual display unit (40) for display, and
 vi. buffers data (33,34,36) for further processing or forwarding to later processing units.

Certain steps undertaken by the main processing unit (32) may occur in parallel, others must occur in series.

In step (i) incoming data (33) is received by the main processing unit (32) and, where necessary it is separated and or converted to create formatted data. Formatted data is the required format for further processing, in many cases this is expected to be numerical values representative of the patient data (28).

In step (ii) the incoming data (33) is checked for artefacts, where an artefact is a value which is outside that possible, for example a temperature of 0° C., a heart rate of 1000 or a sudden drop to zero where other variables do not change significantly. If an artefact is detected then this may trigger an audio or visual alert, where the visual alert may be specific indicia displayed on the visual display unit (40). The following limits are examples of those that may be used to determine if the patient data contains artefacts:
 blood pressure (any of b to d) less than about 20 mm Hg;
 systolic blood pressure above about 220 mm Hg;
 Basically if the figure is outside that able to be sustained by a human being as the source, or so far outside that normally encountered as to most likely be an uncommon, rare or unusual aberration, then the data is most likely to be an artefact and as such the data concerned is unreliable and not used for calculations. If an artefact is detected then it may trigger an alert, but it will result in the data concerned not being used for calculations for a predetermined period. This artefact detection can be used to determine if an input device (2) or its connection to the processing unit (3) has failed, or is at least providing suspect data. This again can prevent false alerts being issued.

In step (iii) the formatted data relating to systolic blood pressure (b), a median heart rate (the median of e to g) (mHR) and the pulseoximeter pulse volume (h) is forwarded as R formatted data (34) to an R processing unit (35) for further processing.

In step (iv) the formatted data relating to systolic blood pressure (b) is forwarded as N formatted data (36) to an N processing unit (37) for further processing.

In step (v) the formatted data is further processed and forwarded to a visual display unit (40) as visual data (38). The indicia shown on the visual display unit (40) upon receipt of the visual data (38) could be for example continuously updated graphs, graphs, numerical data, images, words, sentences, icons, three dimensional images, etc, in any colour, monochrome or black and white combination.

In step (vi) the incoming data (33) and/or formatted data, which includes R formatted data (34) and N formatted data (36), is buffered for a predetermined time period. The predetermined time period could be an entire surgical procedure, 2 minutes, 5 minutes 10 seconds or anything in between. The incoming data (33) or formatted data may, in addition to being buffered, be written out to a permanent or semi-permanent log file for storage or analysis.

Please note that in step (iii) where the heart rate is essentially fixed by pacemaker, beta blockers or high dose anaesthesia the heart rate (e, g, h or mHR) may not forwarded for the R-analysis. In this case the R-analysis is carried out on the systolic blood pressure (b) and pulseoximeter pulse volume (h) data.

R Processing:

In the R processing unit (35) the R formatted data (34) is buffered for a predetermined period, at present this is 5 minutes but this is determined by the sampling rate of the input devices (2) and the desire to use 30 data points to calculate a median value. It is felt that a minimum of 10 data points and a minimum time of about 100 seconds of steady state data is necessary. These minimums are not to be combined to determine a minimum sampling period as a trend over a very short period (less than 40 seconds), unless significant, are unlikely to be indicative of a physiologically significant trend and more likely to be just noise.

The buffered R formatted data (34) for the systolic blood pressure (b) is used to calculate the systolic blood pressure median value (bM) this is then compared to the current systolic blood pressure (b), if they are different then this is noted. The systolic blood pressure median value (bM) is the median of the systolic blood pressure (b) values calculated for a BP time period (bT), where the BP time period (bT) is a predetermined time period finishing at the current time. The BP time period (bT) is at present 5 minutes but it is felt that once steady state has been reached this could be as low as 100 seconds.

A predetermined time later, preferably about 10 seconds later, the systolic blood pressure median value (bM) is recalculated and this is compared to the current systolic blood pressure (b), if these are different then this is noted. This step is repeated each predetermined time period. If four consecutive differences occur, where the differences are all in the same direction from the median then this is likely to be a trend rather than a random event.

The buffered R formatted data (34) for the median heart rate (mHR) is used to calculate the median heart rate median value (mHRM) this is then compared to the current median heart rate (mHR), if they are different then this is noted. The median heart rate median value (mHRM) is the median of the median heart rate median values (mHR) calculated for a mHR time period (mHRT), where the mHR time period (mHRT) is a predetermined time period finishing at the current time. The mHR time period (mHRT) is at present 5 minutes but it is felt that once steady state has been reached this could be as low as 100 seconds.

A predetermined time later, preferably about 10 seconds later, the median heart rate median value (mHRM) is recalculated and this is compared to the current median heart rate (mHR), if these are different then this is noted. This step is repeated each predetermined time period. If four consecutive differences occur, where the differences are all in the same direction from the median, then this is likely to be a trend rather than a random event.

Noting that where the heart rate is essentially fixed by pacemaker, beta blockers or high dose anaesthesia the heart rate (e, g, h or mHR) is not forwarded for the R-analysis. In this case the median heart rate (mHR) calculations will not normally be carried out, though another vital sign indicator may be used as an alternative.

The buffered R formatted data (34) for the pulseoximeter pulse volume (h) is used to calculate the pulseoximeter pulse volume median value (hM) this is then compared to the current pulseoximeter pulse volume (h), if they are different then this is noted. The pulseoximeter pulse volume median value (hM) is the median of the pulseoximeter pulse volume (h) values calculated for a PV time period (hT), where the PV time period (hT) is a predetermined time period finishing at the current time. The PV time period (hT)) is at present 5 minutes but it is felt that once steady state has been reached this could be as low as 100 seconds.

A predetermined time later, preferably about 10 seconds later, the pulseoximeter pulse volume median value (hM) is recalculated and this is compared to the current pulseoximeter pulse volume (h), if these are different then this is noted. This step is repeated each predetermined time period. If four consecutive differences occur, where the differences are all in the same direction from the median, then this is likely to be a trend rather than a random event.

If there is a trend for all of:

the systolic blood pressure (b), the median heart rate (the median of e to f) (mHR), and the pulseoximeter pulse volume (h);

then the chance of this being a random event is 1 in 4096. This is because the chance of a value being randomly over or under the median is 50%, so the chance of 4 consecutive values being the same direction is $(1/2)^4=1/16$ (1 chance in 16), and there are three variables where all need to show a trend so $(1/16)^3=1/4096$. If $CO_2$ was also measured and analysed in the same way then this becomes $(1/16)^4=1/65536$.

Please note that it does not matter if the trend for each of the systolic blood pressure (b), the median heart rate (mHR) and the pulseoximeter pulse volume (h) are in different directions from the median, it only matters that there is a trend. For example the systolic blood pressure (h) could be trending downwards whilst the median heart rate (mHR) and pulseoximeter pulse volume (h) are trending up.

At this point in time the mHR time period (mHRT), BP time period (bT) and the PV time period (hT) are all the same time, however it is felt that in some circumstances these may be different.

Now the number of consecutive values required to show a trend does not need to be 4, it could be 3 or more, and it may be different for each variable. The number of consecutive values considered affects the statistical significance of the result and as such this can be adjusted by a user of the monitoring system (1).

The R processing unit (35) output, the R output (41) is forwarded to an A-processing unit (42). The R output (41) can include, the R formatted data (34), any data relating to the calculations carried out by the R processing unit (35).

Just because there is a trend in all of the variables processed in the R processing unit (35) it does not confirm if the trend is clinically significant, and as such to avoid false alerts a systolic blood pressure (b) confirmation test, N processing, is carried out in parallel.

N Processing:

Once steady state data is being received then the N formatted data (36) is buffered by the N processing unit (37) for a predetermined period before processing. Using the buffered N formatted data (36) the change in systolic blood pressure ($\Delta b_{(12)}$) from time 1 (t1) to time 2 (t2) is calculated. Using this change in systolic blood pressure ($\Delta b_{(12)}$) and the value of the systolic blood pressure at time 1 (bt1) the following calculations are carried out:

$$(bt1 - \bar{b})/(SDb) = V1$$

$$(\Delta b_{(12)} - \Delta \bar{b})/(SD\Delta b) = V2$$

Combined blood pressure Indicator (Cbl)=$\sqrt{(V1^2 + V2^2)}$
where
$\bar{b}$=mean systolic pressure from population data;
$\Delta \bar{b}$ is the mean change in systolic blood pressure from population data over the period of time between t1 and t2;
SDb is the standard deviation of the systolic blood pressure from population data;
SD$\Delta$b is the standard deviation of the change in systolic blood pressure from population data over the period of time between t1 and t2; and the preferred time period between t1 and t2 is 30 seconds. But the time period between t1 and t2 could be any time between about 15 seconds and about 150 seconds based on the population data available so far.

The population data was obtained from patients during surgery with Ethical Committee permission for research and this was used to generate the normalised population data. The numbers used for change in systolic blood pressure vary depending on the length of time between t1 and t2 as such $\Delta \bar{b}$ and SD$\Delta$b depend on the time period chosen. These figures can be generated from systolic blood pressure measurements taken during operations when the patient is at steady state by anyone with permission from the Ethical Committee as such specific numbers are not provided.

More detail of this type of processing is described in the paper Statistics Based Alarms from Sequential Physiological Measurements, Harrison M. J and Connor C. W. *Anaesthesia* 2007 62 pages 1015-1023 (incorporated by reference). This paper also describes the use of a Principal Component Analysis which is felt to be a better method but has not yet been implemented, so it could replace the current method.

It should be noted that if the combined blood pressure Indicator (Cbl) is greater than 2 then this is considered statistically significant, though without confirmation by a clinician it may not be clinically significant. The trigger point for the combined blood pressure Indicator (Cbl) value can be adjusted by a user of the monitoring system (1), though it is felt that for most cases a minimum of 2 should be used.

This test performed by the N processing unit (37) indicates that a significant change has taken place in the variable, in this case systolic blood pressure (b). It does not provide any information useful to a clinician suggesting what that significant change means or if it is clinically significant.

The output from the N processing unit (37), the N output (43), is forwarded to the A processing unit (42). The N output (43) can include, the N formatted data (36), any data relating to the calculations carried out by the N processing unit (37) and the combined blood pressure indicator (Cbl).

A processing

The A processing unit (42) confirms:
there is a trend for each of the systolic blood pressure (b), the median heart rate (mHR) and the pulseoximeter pulse volume (h); and
that the combined blood pressure Indicator (Cbl) is 2 or greater;
if they are then the A processing unit (42) carries out further processing prior to issuing an alert (50). By only issuing an alert (50) if the required conditions are met there is a high likelihood that a clinically significant change has occurred, and that the alert (50) is likely to be true. The number of false alerts, that is alerts issued that do not need to be followed up by a clinician, are expected to be well below current levels by using this system and/or method.

This further processing can include comparing the direction of the trends with those expected for certain conditions, checking the magnitude of the change in blood pressure against predetermined values, checking to see if an alert (50) was issued previously, or checking input data (33) and/or N output (43) and/or R output (41) against predetermined stored values for example.

This alert (50) can take many forms, it may be any recognisable visual, audio or vibrational/tactile signal able to be interpreted by a user. For example it could be one or more indicia sent to the visual display unit (40), an audible signal from a headset or speaker, a specific lamp (LED, incandescent, fluorescent), a signal to vibrate sent to a pager, or any combination of these sent to an alert device (51). Where the alert device (51). is a device that makes the alert audible and/or visually accessible and/or accessible in a tactile manner. That is the alert device (51) is for example the headset, speaker, lamp, pager, vibrator, monitor, etc, or any combination of these. The alert device (51) and/or visual display unit (40) is connected to the processing unit physically or wirelessly (radio frequency, optically etc).

In some cases the clinician may wear a Bluetooth™ headset and the processing unit (3) transmits an alert (50) to the headset, this alert (50) could be a verbal description of the alert (50) or simply a recognisable sound/sound combination. This could be supported by the monitor displaying a series of indicia representing the direction of the trend of each of the variables along with a written description of a possible reason for the alert (50).

In a second embodiment the incoming data is fed to a computer running a piece of software that carries out the calculation steps, determines the indicia to display and outputs this to a standard monitor. The incoming data (33) may need to be processed into a suitable form for the software and this may be accomplished by standard hardware components, standard or custom written drivers, or other known means.

If raw data is sent through then the processing unit (3) may need to incorporate drivers or other pre-processing steps, or units to convert the data received into a usable format.

In alternative embodiments step (v) carried out in the main processing unit (32) may use the incoming data (33) without prior processing into formatted data.

In further alternative embodiments the R-formatted data (34) includes one or more additional data streams selected from temperature, gas concentrations and respiratory rate (a, i, j, k, l) which are also subject to similar analysis to determine a trend. That is, the buffered R formatted data (34) for variable q (q) is used to calculate the median q value (qM) this is then compared to the current value of the q variable (q), if they are different then this is noted. The median q value (qM) is the median value of the variable q (q) values calculated for a qV time period (qT), where the qV time period (qT) is a predetermined time period finishing at the current time. The qV time period (qT) is at present 5 minutes but it is felt that once steady state has been reached this could be as low as 100 seconds. A predetermined time later, preferably about 10 seconds later, the median q value (qM) is recalculated and this is compared to the current value of the variable q (q), if these are different then this is noted. This step is repeated each predetermined time period. If four consecutive differences occur, where the differences are all in the same direction from the median, then this is likely to be a trend.

In still further embodiments the anaesthesia monitor (27) is incorporated into the processing unit (3) which then displays any or all of the raw and processed data (real time or otherwise) along with the alerts.

In further embodiments the mean blood pressure (d), and change in mean blood pressure between time 1 (t1) and time 2 (t2), ($\Delta d_{(12)}$), is used instead of the systolic blood pressure (b) and change in systolic blood pressure (b) between t1 and t2, ($\Delta b_{(12)}$). In this case the population values for the mean blood pressure must be used for the R processing steps.

In further embodiments a specific source for the heart rate, any one of ECG heart rate (e), blood pressure monitor heart rate (f) or pulseoximeter heart rate (g) is used rather than the median heart rate (mHR). In other embodiments other combinations of ECG heart rate (e), blood pressure monitor heart rate (f) and pulseoximeter heart rate (g) are used, for example a mean value could be calculated and used.

Please note that at present the pulseoximeter pulse volume (h) is used but an alternative source of pulse volume data could be used if available.

In some embodiments only the blood pressure (b and/or d), a heart rate (one or more of e, f, g or the median of e to g) and the pulseoximeter pulse volume (h) are inputs, this is because even though the gas analysis monitor (26) is not present the method and monitoring system (1) can still operate. In this case the stable state required for the calculations will most likely need to be determined by the clinician.

The range of input devices (2) and data collected is very wide and those mentioned earlier should not be seen as limiting, for example there are at least the following:

SpO2 (from pulseoximeter)—blood oxygenation;
ST changes from the ECG (shows signs of hypoxia in the heart muscle);
Cardiac output monitors using many different techniques (pulsecontour analysis, thermal dilution, dye dilution, impedance, Doppler, suprasystolic waveform analysis etc.);
Cerebral function monitors (BIS, Evoked potentials, infrared spectroscopy, arterial-venous difference); T
Transcutaneous $O_2/CO_2$ analysis, haemoglobin assessment;
Respiratory physiology measurements (pressure volume loops, resistance of airways, $O_2$ difference to detect changes in metabolic rate);
Neuromuscular monitoring devices to detect muscle relaxation;
Echocardiography;
Intravascular measurement of electrolytes, chemicals and certain drugs (field effect transducers); and
Near real-time measurement of blood clotting.

The output from any of the above could also undergo R analysis

It should be noted that it is believed that the best results from the R analysis are obtained by using a median value, however, this does not preclude the use of a calculated mean or predetermined population value instead. The mean value for the variable concerned could be calculated at a specific time, or after a specific number of measurements have been taken, or it could be continually updated. As such where the term 'median' is used it is intended to also include the use of a predetermined population value or a calculated mean value instead of the median.

Figure 3:
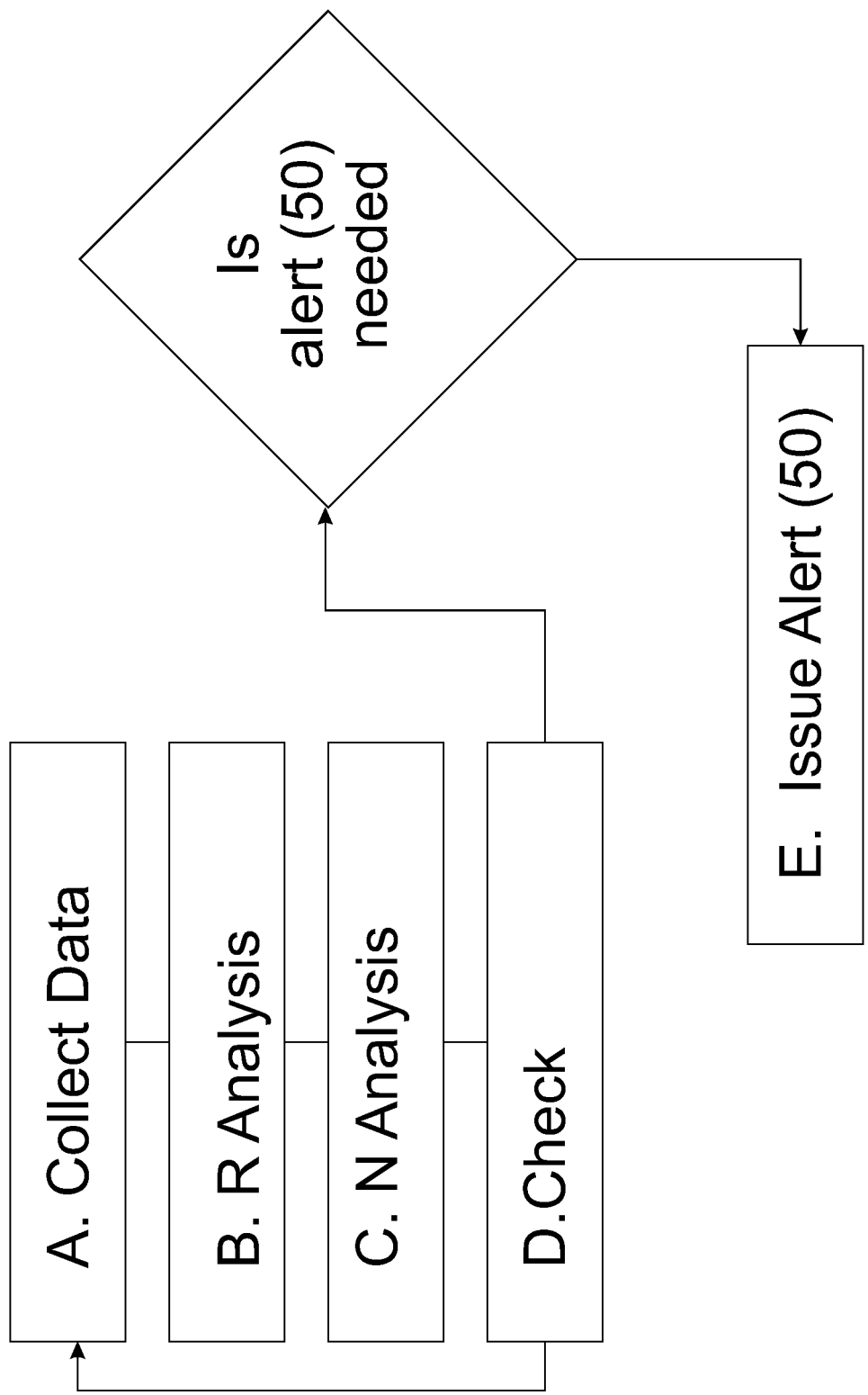
FIG. 3 is a flowchart showing the method

The invention also includes a method of analysing physiological data received from at least two input devices (2) as shown in FIG. 3, which includes the following steps:

A. Collect data;
B. R Analysis;
C. N Analysis;
D. Check;
E. Is an alert (50) necessary:
F. Issue Alert (50).

Where step A is the collection of data from the input devices (2) and conversion, where necessary, into a form able to be processed further.

After step A, steps B and C, the R analysis and N analysis respectively, as described above in detail, are carried out. The R output (41) and the N output (43) are then forwarded to the A processing unit (42) for checking.

In step D the A processing unit (42) confirms that there is a statistically significant trend in the separate data streams processed by the R processing unit (35), and that the combined blood pressure indicator (Cbl) confirms a statistically significant change in blood pressure (b or d) and change in blood pressure ($\Delta b_{(12)}$ or $\Delta d_{(12)}$. If both the R output (41) and the combined blood pressure (Cbl) show a statistically significant result then the A processing unit (42) issues an alert (50).

Please see some examples below, noting that although an alert (50) is issued and the trends are present the clinician needs to confirm the presence of the condition:—

Example 1

Downward trend in systolic blood pressure (b);
Upward trend in the median heart rate (mHR); and
Downward trend in the pulseoximeter pulse volume (h); and Cbl>SS;
could indicate acute onset hypovolaemia.(absolute).

Example 2

Downward trend in systolic blood pressure (b);
variable trend in the median heart rate (mHR); and
upward trend in the pulseoximeter pulse volume (h); and Cbl>SS;
could indicate acute onset hypovolaemia (relative);

Example 3

Upward trend in systolic blood pressure (b);
upward trend in the median heart rate (mHR); and downward trend in the pulseoximeter pulse volume (h); and CbI>SS;
could indicate a sympathetic response;

Key

1. Monitoring system;
2. Input devices;
3. Processing unit;
4. Output unit;
5. ;
23. Electrocardiogram (ECG);
24. Blood pressure monitor;
25. Pulseoximeter;
26. Gas analysis monitor;
27. Anaesthesia monitor;
28. Patient data;
30. ;
31. first processing unit;
32. main processing unit;
33. incoming data (to main processing unit, includes 28 and RAPPV where calculated);
34. R formatted data (b and e to i)
35. R processing unit;
36. N formatted data (b);
37. N processing unit;
38. Visual data;
39. ;
40. Visual display unit;
41. R output (output from the R processing unit);
42. A processing unit;
43. N output (output from the N processing unit);
50. Alert;
a. temperature;
b. systolic blood pressure;
c. diastolic blood pressure;
d. mean blood pressure;
e. ECG heart rate;
f. Blood pressure monitor heart rate;
g. pulseoximeter heart rate;
h. pulseoximeter pulse volume;
i. gas end tidal (gas Et) $CO_2$;
j. gas inspired (gas Fi) $CO_2$;
k. gas respiration rate;
l. gas end-tidal fraction of anaesthetic agent;
bM. Median systolic blood pressure over time period bT;
bT. Blood pressure time period;
mHR. Median Heart Rate, median of e to g;
mHRM. median heart rate median value over time mHRT;
mHRT. median heart rate time period;
hM. pulseoximeter pulse volume median value over time period hT;
hT. pulseoximeter pulse volume time period;
q. variable q refers to any measured variable except b, mHR and h;
qM median value of the q variables over time qT;
qT variable q time period;
t1 time 1;
t2 time 2;
$\Delta b_{(12)}$ change in systolic blood pressure (b) between t1 and t2;
$(\Delta \bar{b})$ mean change in systolic blood pressure between t1 and t2 from population data.
$\bar{b}$=mean systolic pressure from population data;
CbI Combined blood pressure Indicator.
$\Delta d_{(12)}$ change in mean blood pressure (d) between t1 and t2;
ut1 is a value of the primary physiological variable at t1;
$\bar{u}$ is a mean primary physiological value from population data;
$\Delta \bar{u}$ is a mean change in the primary physiological variable from the population data over the period of time between t1 and t2;
$\Delta u_{(12)}$ is a change in the primary physiological variable over the period of time between t1 and t2;
SDu is the standard deviation of the primary physiological variable from the population data;
SD$\Delta$u is the standard deviation of the change in primary physiological variable from the population data over the period of time between t1 and t2;
CuI is a combined primary physiological variable indicator;

The invention claimed is:

1. A system for monitoring a medical patient's condition, comprising:
at least one input device, a processing unit and one or more output units, wherein
the or each input device is configured to measure at least one physiological variable and send a physiological variable input to the processing unit, and wherein one said input device is a blood pressure monitor configured to measure systolic or mean blood pressure;
the processing unit is configured to directly or indirectly accept each physiological variable input from the or each input device and carry out a method for issuing an alert which includes the following steps:
carry out an R analysis on two or more physiological variable inputs;
carry out an N analysis on a primary physiological variable input;
issue an alert if the R analysis confirms a trend for each of the physiological variable inputs and the N analysis shows a statistically significant change in the primary physiological variable input;
wherein the two or more physiological variable inputs include systolic or mean blood pressure and pulse volume, and the primary physiological variable input is systolic or mean blood pressure;
and the R-analysis includes the following steps in order:
i. buffer each physiological variable input for a physiological variable R time period, where the physiological variable R time period finishes at a current time, creating buffered physiological variable data for each vital sign input;
ii. determine a physiological variable median from each set of buffered physiological variable data;
iii. compare a current physiological variable value, which is the physiological variable input at the current time, with the respective physiological variable median to determine a physiological variable difference for each physiological variable;
iv. wait a predetermined time, a physiological variable R2 time interval, and carry out steps (i) to (iii) until at least 3 physiological variable differences for each physiological variable have been calculated;
v. compare each physiological variable difference for each physiological variable and if three or more consecutive physiological variable differences for each physiological variable input are in the same direction from the respective physiological variable median then a trend is confirmed;
such that for the R-analysis each physiological variable R time period includes at least 10 measurements of the physiological variable in question and the physiological variable R time period is at least 100 seconds, and the N-analysis includes either steps (vi) to (viii) in order, or steps (ix) and (x) in order:

vi. buffer the primary physiological variable input for a primary physiological variable N time period, where the primary physiological variable N time period finishes at the current time, creating buffered primary data;

vii. carry out the following calculations:

$$(ut1-\bar{u})/(SDu)=V1$$

$$(\Delta u_{(12)}-\Delta\bar{u})/(SD\Delta u)=V2$$

$$CuI=\sqrt{(V1^2+V2^2)}$$

where t1=time 1;

t2=current time;

ut1 is a value of the primary physiological variable at t1;

$\bar{u}$ is a mean primary physiological value from population data;

$\Delta \bar{u}$ is a mean change in the primary physiological variable from the population data over the period of time between t1 and t2;

$\Delta u_{(12)}$ is a change in the primary physiological variable over the period of time between t1 and t2;

SDu is the standard deviation of the primary physiological variable from the population data;

SDΔu is the standard deviation of the change in primary physiological variable from the population data over the period of time between t1 and t2;

CuI is a combined primary physiological variable indicator;

viii. compare CuI value with a predetermined value SS, if CuI>SS then this confirms a statistically significant change in the primary physiological variable;

such that for steps (vi) to (viii) the N-analysis SS is at least 1, and the time period between t1 and t2 is at least 10 seconds;

ix. buffer the primary physiological variable input for a primary physiological variable N time period, where the primary physiological variable N time period finishes at the current time, creating buffered primary data;

x. carry out a principal component analysis to determine whether, over the time period t2-t1, a statistically significant change has occurred in the primary physiological variable, where t1=time 1, and t2=current time; wherein a statistically significant change has occurred if the principal component analysis confirms that the primary physiological variable is greater than a predetermined number of standard deviations (SS) from that expected in each direction, such that SS is independently chosen for each direction;

such that for steps (ix) and (x) the N-analysis using the principal component analysis method the time period between t1 and t2 is at least 10 seconds and each SS is greater than or equal to 1; wherein:

the processing unit is further configured to output the alert as an alert signal to the or each output unit; and the or each output unit is configured to process the alert signal into an alert output for a user in one or more of the following forms visual, audio, vibratory, or tactile.

2. The system as claimed in claim 1, wherein the or each value SS is equal to or greater than 2.

3. The system as claimed in claim 1, wherein the R-analysis is carried out on at least three physiological variables.

4. The system as claimed in claim 3, wherein one of the physiological variables is heart rate, except where the heart rate is being stabilised by mechanical, electro-mechanical or chemical means, or a combination of these.

5. The system as claimed in claim 4, wherein the heart rate is a median heart rate obtained from three or more different heart rate sources.

6. The system as claimed in claim 1, wherein each physiological variable R time period includes at least 20 measurements of the physiological variable in question.

7. The system as claimed in claim 6, wherein each physiological variable R time period includes at least 30 measurements.

8. The system as claimed in claim 1, wherein the physiological variable R time period is between 100 seconds and 5 minutes.

9. The system as claimed in claim 1, wherein the physiological variable R2 time interval is at least 10 seconds.

10. The system as claimed in claim 1, wherein the time period between t1 and t2 is between 15 seconds and 150 seconds.

11. The system as claimed in claim 1, wherein the or each input device is selected from the list consisting of an electrocardiogram (ECG), a temperature monitor, a pulse-oximeter, a non-invasive blood pressure monitor, an invasive blood pressure monitor, a gas analysis monitor, and an anaesthesia monitor connected to one or more of the previously mentioned input devices.

12. The system as claimed in claim 1, wherein the processing unit is configured to directly accept the output from the or each input device.

13. The system as claimed in claim 1, wherein the processing unit is configured to check each physiological variable input against one or more predetermined value, an artifact value, for that physiological variable input to determine if that physiological variable input is an artifact, where an artifact is a physiological variable input outside that possible for a patient at that time, if an artifact is detected then that physiological variable data is not used for the R-analysis or N-analysis.

14. The system as claimed in claim 13, wherein if an artifact is detected then an artifact alert is issued.

15. The system as claimed in claim 13, wherein the processing unit is configured to suppress equivalent alerts for a predetermined period of time, an alert suppression time.

16. The system as claimed in claim 15, wherein the alert suppression time is 5 minutes.

17. The system as claimed in claim 1, wherein one output device is a visual display unit configured to visually display a representation of the alert.

18. The system as claimed in claim 17, wherein the visual display unit also displays a representation of the physiological variable input for one or more physiological variable.

19. The system as claimed in claim 18, wherein the representation is one or more forms selected from the list consisting of icons, words, graphs, colours, visual indicia and combinations of these.

20. The system as claimed in claim 1, wherein one output device is a headset configured to deliver an audio alert.

21. The system as claimed in claim 20, wherein the headset is wirelessly connected to the processing unit.

22. The system as claimed in claim 1, wherein one output device is a speaker configured to deliver an audio alert.

23. The system as claimed in claim 20, wherein the audio alert includes an audio description of the alert.

24. A processing unit configured for use as the processing unit in the system as claimed in claim 1 that is configured to be connected, wirelessly or otherwise, to one or more input devices and one or more output devices.

25. The system as claimed in claim 22, wherein the audio alert includes an audio description of the alert.

* * * * *